United States Patent
Nitta

(10) Patent No.: US 10,974,011 B2
(45) Date of Patent: Apr. 13, 2021

(54) FILTER STRUCTURE

(71) Applicant: METRAN CO., LTD., Kawaguchi (JP)

(72) Inventor: Kazufuku Nitta, Kawaguchi (JP)

(73) Assignee: Metran Co., Ltd., Kawaguchi (JP)

( * ) Notice: Subject to any disclaimer, the term of this patent is extended or adjusted under 35 U.S.C. 154(b) by 994 days.

(21) Appl. No.: 15/107,016

(22) PCT Filed: Dec. 25, 2014

(86) PCT No.: PCT/JP2014/084243
§ 371 (c)(1),
(2) Date: Jun. 21, 2016

(87) PCT Pub. No.: WO2015/099011
PCT Pub. Date: Jul. 2, 2015

(65) Prior Publication Data
US 2017/0028157 A1    Feb. 2, 2017

(30) Foreign Application Priority Data
Dec. 26, 2013 (JP) .............................. JP2013-268195

(51) Int. Cl.
*A61M 16/10* (2006.01)
*A61M 16/06* (2006.01)
(Continued)

(52) U.S. Cl.
CPC .... *A61M 16/1055* (2013.01); *A61M 16/0066* (2013.01); *A61M 16/06* (2013.01);
(Continued)

(58) Field of Classification Search
CPC  F04D 29/601; F04D 29/703; A61M 16/0066; A61M 16/105; A61M 16/047;
(Continued)

(56) References Cited

U.S. PATENT DOCUMENTS

| 4,197,841 A | * | 4/1980 | Brauer | .................. A62B 18/08 |
| | | | | 128/201.13 |
| 5,054,479 A | * | 10/1991 | Yelland | ..................... A61F 9/02 |
| | | | | 128/201.25 |

(Continued)

FOREIGN PATENT DOCUMENTS

| CN | 1483482 A | 3/2004 |
| CN | 2607152 Y | 3/2004 |

(Continued)

OTHER PUBLICATIONS

Office Action of Chinese Patent Office issued in Chinese Application No. 201480071184.9 dated Jan. 24, 2018 (6 pages).

(Continued)

*Primary Examiner* — Tu A Vo
*Assistant Examiner* — Alexander Morales
(74) *Attorney, Agent, or Firm* — Flynn Thiel, P.C.

(57) ABSTRACT

A filter structure includes a blower having a gas suction opening, the blower compressing gas taken from the gas suction opening and supplying the compressed gas to respiratory organs of a patient; a housing that contains the blower and has air passage openings connected to the gas suction opening; a bag at least part of which is made of a nonwoven paper as a filter material, for covering the housing; and a chamber forming member disposed between the housing and the bag, for forming a chamber CAM between each air passage opening and the nonwoven paper. Thus, effort for maintenance of a filter is reduced.

6 Claims, 4 Drawing Sheets

(51) Int. Cl.
*A61M 16/00* (2006.01)
*F04D 17/16* (2006.01)
*F04D 29/70* (2006.01)
*F04D 29/60* (2006.01)

(52) U.S. Cl.
CPC .......... *A61M 16/107* (2014.02); *F04D 17/16* (2013.01); *F04D 29/601* (2013.01); *F04D 29/703* (2013.01); *A61M 2205/7509* (2013.01); *A61M 2205/7518* (2013.01); *A61M 2205/7536* (2013.01); *A61M 2205/7545* (2013.01)

(58) Field of Classification Search
CPC .. A61M 16/06; A61M 16/22; A61M 2205/75; A61M 2205/7509; A61M 2205/7518; A61M 2005/1657; A62B 23/00; A62B 23/02; A62B 23/025; A62B 7/10
See application file for complete search history.

(56) References Cited

U.S. PATENT DOCUMENTS

| | | | | |
|---|---|---|---|---|
| 5,104,430 | A * | 4/1992 | Her-Mou | A62B 18/006 128/205.29 |
| 5,372,130 | A * | 12/1994 | Stern | A62B 18/006 128/205.25 |
| 5,592,936 | A * | 1/1997 | Thomas, Jr. | A41D 13/11 128/201.24 |
| 6,014,971 | A * | 1/2000 | Danisch | A62B 18/045 128/201.25 |
| 6,257,235 | B1 * | 7/2001 | Bowen | A62B 23/025 128/206.12 |
| 8,951,322 | B2 | 2/2015 | Pfannenberg et al. | |
| 9,498,656 | B2 * | 11/2016 | Elliott | A62B 7/08 |
| 9,950,197 | B2 * | 4/2018 | Volmer | F04B 27/004 |
| 2003/0155757 | A1 * | 8/2003 | Larsen | B60R 21/2644 280/741 |
| 2003/0192541 | A1 * | 10/2003 | Avery | A62B 17/006 128/204.18 |
| 2005/0034724 | A1 | 2/2005 | O'Dea | |
| 2005/0103339 | A1 * | 5/2005 | Daly | A61M 16/0057 128/204.18 |
| 2007/0101867 | A1 | 5/2007 | Hunter et al. | |
| 2007/0102280 | A1 | 5/2007 | Hunter et al. | |
| 2007/0163588 | A1 | 7/2007 | Hebrank et al. | |
| 2008/0216831 | A1 * | 9/2008 | McGinnis | B62J 9/26 224/148.2 |
| 2009/0004047 | A1 | 1/2009 | Hunter et al. | |
| 2009/0031681 | A1 * | 2/2009 | Linhart | B01D 46/02 55/368 |
| 2010/0083967 | A1 * | 4/2010 | Kuriyama | A62B 9/006 128/204.23 |
| 2012/0174922 | A1 * | 7/2012 | Virr | A62B 18/006 128/205.25 |
| 2013/0112201 | A1 * | 5/2013 | Graham | A61M 16/0875 128/203.27 |
| 2014/0137870 | A1 * | 5/2014 | Barlow | A61M 16/0057 128/205.25 |
| 2014/0216479 | A1 * | 8/2014 | Jeong | A41D 13/1138 128/863 |
| 2014/0261425 | A1 * | 9/2014 | Connor | A62B 18/045 128/201.25 |

FOREIGN PATENT DOCUMENTS

| | | |
|---|---|---|
| CN | 101158364 A | 4/2008 |
| JP | 2003-500178 A | 1/2003 |
| JP | 2010-504170 A | 2/2010 |
| JP | 2011-120853 A | 6/2011 |
| JP | 2013-71004 A | 4/2013 |
| JP | 5211302 B1 | 6/2013 |
| WO | WO 2011/022779 A1 | 3/2011 |
| WO | WO 2012/174602 A1 | 12/2012 |
| WO | WO 2013/133889 A1 | 9/2013 |

OTHER PUBLICATIONS

Search Report of European Patent Office issued in Application No. 14873133 dated Nov. 22, 2016 (6 pages).
Notification of Transmittal of International Search Report issued in Application No. PCT/JP2014/084243 dated Feb. 3, 2015 (2 pages).
International Search Report issued in Application No. PCT/JP2014/084243 with English translation dated Feb. 3, 2015 (5 pages).
Written Opinion of International Searching Authority issued in Application No. PCT/JP2014/084243 dated Feb. 3, 2015 (4 pages).

* cited by examiner

FILTER STRUCTURE

TECHNICAL FIELD

The present invention relates to a filter structure for a blower.

BACKGROUND ART

Sleep apnea is caused by a root of a tongue and a soft palate moving down due to flaccid muscles during sleep and clogging a trachea. Patients with this respiration disorder use respiratory assistance devices, which prevent the clogging by the application of a positive pressure to the trachea (refer to Japanese Patent Application Laid-Open No. 2013-071004).

The respiration assistance devices are provided with a blower having a gas suction opening. The blower compresses gas such as air taken from the gas suction opening, and supplies the compressed gas to the trachea of the patient. In the blower, a filter is attached to the gas suction opening in order to prevent the contamination of bacteria, viruses, and dust into inspiratory gas.

SUMMARY OF INVENTION

Technical Problem

However, since the gas suction opening is not large in size, neither is the filter attached to the gas suction opening, and therefore the filter is easily clogged. The clogged filter degrades the performance of the blower, and interferes with the supply of a sufficient amount of gas to the trachea of the patient, thus failing to prevent the clogging of the trachea. That is to say, the apnea may occur even with a treatment using the respiratory assistance device. In order to avoid such a risk, maintenance including filter replacement is required on a regular basis. Depending on a usage environment, the frequency of the filter maintenance is increased, thus expending much effort.

The present invention has been made in consideration of the above problem, and an object thereof is to provide a filter structure that reduces effort required for maintenance of a filter.

Solution to Problem (1) The present invention is a filter structure characterized by including: a blower having a gas suction opening, the blower compressing gas taken from the gas suction opening and supplying the compressed gas to respiratory organs of a user; a housing that contains the blower and has an air passage opening connected to the gas suction opening; a bag at least part of which is made of a filter material, the bag covering the housing; and a chamber forming member disposed between the housing and the bag, the chamber forming member forming a chamber between the air passage opening and the filter material.

According to the present invention, it is possible to significantly increase the size of a filter. Thus, even if part of the filter is clogged, a sufficient amount of gas can be supplied to the trachea of a user without degrading the performance of the blower. Thus, the partial clogging of the filter does not require maintenance of the filter. In other words, it is possible to reduce effort for the maintenance of the filter.

Since the bag made of the filter material covers the entire device, the device is protected from bacteria, viruses, and dirt.

Patterning or coloring the exterior of the bag serves to improve a bag design. As a result, it is possible to get rid of a negative image as a medical appliance. This brings the user an easy feeling about use. Thus, a product's value rises.

(2) The present invention is also a filter structure described in the above (1) and characterized in that the bag is formed by closing an opening, and replaceable.

The above-described invention allows easy replacement of the filter. As a result, it is possible to further reduce the effort for the maintenance of the filter.

Replacement among a plurality of types of bags having different patterns or colors serves to change the image of a product. As a result, the product's value further rises.

(3) The present invention is also a filter structure described in the above (2) and characterized in that the opening is openable and reclosable.

According to the above-described invention, the filter can be detached and cleaned. As a result, it is possible to further reduce the effort for the maintenance of the filter.

(4) The present invention is a filter structure characterized by including a mask at least part of which is made of a filter material, the mask covering a mouth or nose of a user so as to form a chamber between the mask and a face of the user; and a blower that is provided in the chamber and has a gas suction opening for taking gas inside the chamber, the blower compressing the gas taken through the gas suction opening and supplying the compressed gas to respiratory organs of the user.

(5) The present invention is a filter structure characterized by including a mask covering a mouth or nose of a user; a blower that is provided to the mask and has a gas suction opening for taking gas from the outside of the mask, the blower compressing the gas taken through the gas suction opening and supplying the compressed gas to respiratory organs of the user through the inside of the mask; a cover at least part of which is made of a filter material, the cover covering the mask; and a chamber forming member disposed between the mask and the cover, the chamber forming member forming a chamber between the gas suction opening and the filter material.

According to the invention described in the above-described (4) and (5), it is possible to significantly increase the size of a filter. Thus, even if part of the filter is clogged, a sufficient amount of gas can be supplied to the trachea of a user without degrading the performance of the blower. Thus, the partial clogging of the filter does not require maintenance of the filter. In other words, it is possible to reduce effort for the maintenance of the filter.

(6) The present invention is a filter structure according to any one of the above (1) to (5) and characterized in that the filter material is a nonwoven paper.

The invention described above results in a reduction in manufacturing costs.

The exterior of the bag can be easily patterned or colored by printing on the nonwoven paper without a cost increase. That is to say, a bag design is easily improved.

Advantageous Effects of Invention

The filter structure described in the above (1) to (6) of the present invention has the superior effect of reducing effort for maintenance of the filter.

DESCRIPTION OF EMBODIMENTS

A respiratory assistance device according to the present invention will be hereinafter described in detail with reference to the drawings.

First Embodiment

Figure 1:
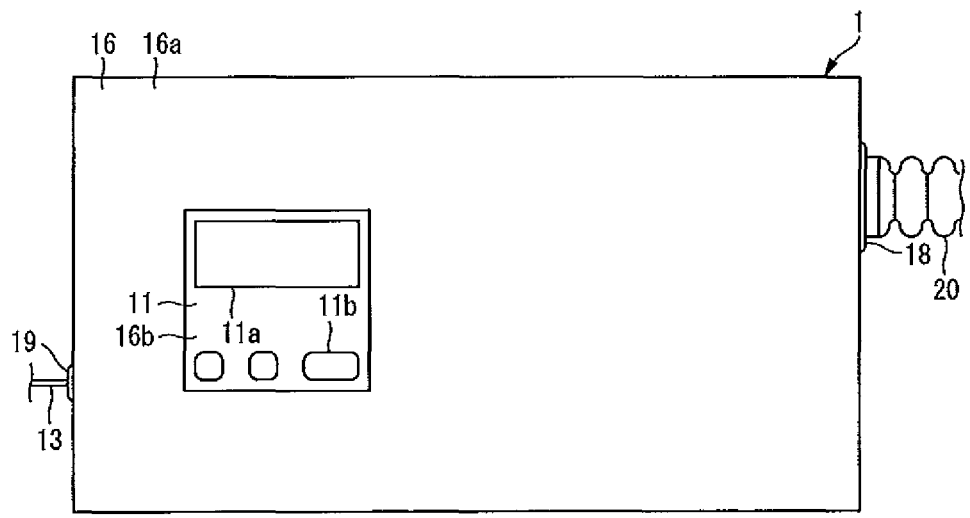
FIG. 1 is an external view of a respiratory assistance device that adopts a filter structure according to a first embodiment of the present invention.
Figure 2:
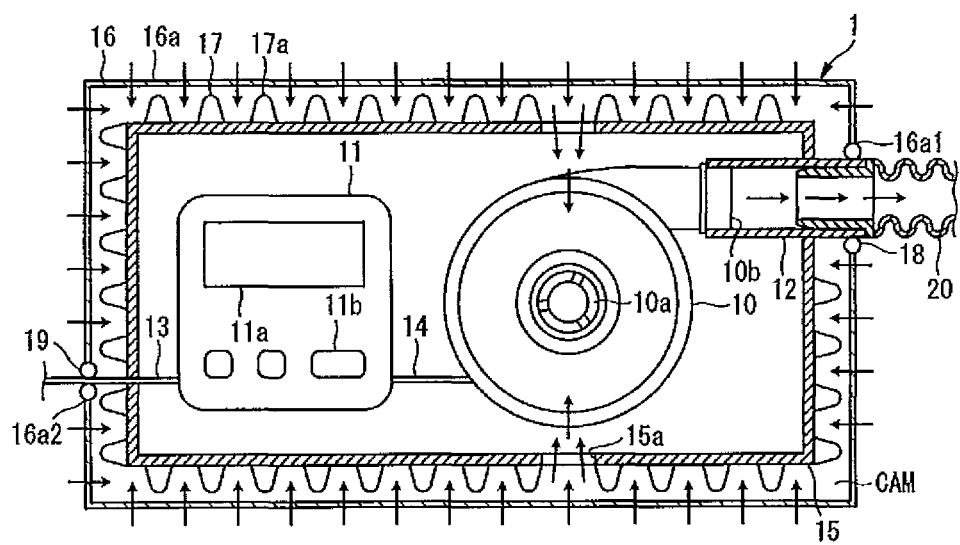
FIG. 2 is a schematic view illustrating the inside of the respiratory assistance device illustrated in FIG. 1.

First, the structure of a respiratory assistance device 1 that adopts a filter structure according to an embodiment of the present invention will be described with reference to FIGS. 1 and 2. FIG. 1 is an external view of the respiratory assistance device 1. FIG. 2 is a schematic view illustrating the inside of the respiratory assistance device 1. Note that, part of the structure is appropriately omitted in each of these and subsequent drawings to simplify the drawings.

The respiratory assistance device 1 illustrated in FIGS. 1 and 2 is used by a patient (user) of a respiration disorder to generate a positive pressure in his/her trachea. More specifically, the respiratory assistance device 1 includes a blower 10, a control box 11, an air feed pipe 12, a power code 13, a connection code 14, a housing 15, a bag 16, a chamber forming member 17, O-rings 18 and 19, and the like.

The blower 10 is contained in the housing 15. The blower 10 is controlled by a control unit (not shown) in the control box 11. That is, the blower 10 is operated under the control of the control unit, and the control unit manages an operation state thereof. The blower 10 has a gas suction opening 10a, an air feed opening 10b, and the like. The blower 10 compresses gas such as air taken through the gas suction opening 10a, and supplies the compressed gas to respiratory organs of the patient through the air feed opening 10b and the like. Note that, the blower 10 has a well-known structure and hence the detailed description thereof will be omitted using, for example, Japanese Patent No. 5211302 as the reference.

The control box 11 is contained in the housing 15. The control box 11 is provided with a monitor 11a, buttons 11b, and the like. The control box 11 contains the control unit (not shown). The monitor 11a is, for example, a liquid crystal display to display an operation state of the respiratory assistance device 1. The buttons 11b function as a man-machine interface by the operation of which predetermined signals are inputted to the control unit. The control unit is operated by power supplied from the power code 13. The control unit performs various controls in response to the predetermined signals inputted by the operation of the buttons 11b. To be more specific, the control unit includes a CPU, a RAM, a ROM, and the like. The CPU is a so-called central processing unit, which executes various programs to implement various functions. The RAM is used as work space for the CPU. The ROM stores a basic OS and the programs executed by the CPU.

The air feed pipe 12 is provided so as to penetrate the housing 15 and the bag 16. The air feed pipe 12 is connected to the air feed opening 10b of the blower 10 at its proximal end, and connected to a duct 20 in a detachable manner at its distal end. The air feed pipe 12 leads the gas fed from the air feed opening 10b of the blower 10 into the duct 20. The power code 13 extends from the control box 11 so as to penetrate the housing 15 and the bag 16. Through the power code 13, the control unit (not shown) in the control box 11 is powered from outside.

The connection code 14 electrically connects between the control unit (not shown) in the control box 11 and a motor (not shown) in the blower 10. Through the connection code 14, an electric signal is sent from the control unit to the motor.

The housing 15 contains the blower 10, the control box 11, the air feed pipe 12, and the like. The housing 15 is formed with air passage openings 15a and the like. The air passage openings 15a are formed for the purpose of taking the air, which is to be taken into the blower 10, from the outside of the housing 15 to the inside thereof. A plurality of projections 17a, which constitute the chamber forming member 17, are attached to the outside of the housing 15.

The bag 16 for covering the housing 15 is made of a nonwoven paper 16a having an opened window (with no reference numeral), and a transparent film 16b for closing the window formed in the nonwoven paper 16a. The nonwoven paper 16a functions as a filter. In the nonwoven paper 16a, a hole 16a1 is formed to pass the air feed pipe 12, and a hole 16a2 is formed to pass the power code 13. The O-rings 18 and 19 are fitted into the holes 16a1 and 16a2, respectively. Note that, the bag 16 is formed by closing an opening (not shown) and replaceable. The opening of the bag 16 is openable and reclosable. At least part of the bag 16 may be formed of the nonwoven paper 16a. Also, the exterior of the bag 16 may be patterned or colored. The bag 16 does not pass gas except for the portion of the nonwoven paper 16a.

The chamber forming member 17 is present between the housing 15 and the bag 16, and forms a chamber CAM between each air passage opening 15a of the housing 15 and the nonwoven paper 16a constituting the bag 16. The chamber forming member 17 is constituted by the plurality of projections 17a attached to the outside of the housing 15.

The O-rings 18 and 19 are fitted on the holes 16a1 and 16a2 formed in the nonwoven paper 16a, respectively. Into the O-ring 18, the air feed pipe 12 is fitted. Into the O-ring 19, the power code 13 is fitted.

The duct 20 leads the gas fed through the air feed pipe 12 to the respiratory organs of the patient.

Next, a gas flow in the respiratory assistance device 1 will be described with reference to FIG. 2.

Upon operating the blower 10, gas outside the bag 16 is taken into the chamber CAM formed inside the bag 16 through the nonwoven paper 16a. The gas taken into the chamber CAM is taken into the housing 15 through the air passage openings 15a.

The gas taken into the housing 15 is taken into the blower 10 through the gas suction opening 10*a*. The gas taken into the blower 10 is compressed and supplied to the respiratory organs of the patient through the air feed opening 10*b*, the air feed pipe 12, the duct 20, and the like.

As described above, the filter structure that the respiratory assistance device 1 adopts allows a significant increase in the area of the filter. Thus, even if part of the nonwoven paper 16*a*, used as the filter, is clogged, a sufficient amount of gas can be supplied to the trachea of the patient without degrading the performance of the blower 10. Therefore, even if part of the nonwoven paper 16*a* is clogged, the nonwoven paper does not require maintenance. In other words, it is possible to reduce effort for the maintenance of the nonwoven paper 16*a*.

Since the bag 16 made of the nonwoven paper 16*a* covers the entire device, the device can be protected from bacteria, viruses, and dirt.

Patterning or coloring the exterior of the bag 16 serves to improve a bag design. As a result, it is possible to get rid of a negative image as a medical appliance. This brings the patient an easy feeling about use. Thus, a product's value rises.

Furthermore, since the bag 16 is formed by closing the opening (not shown) and replaceable, the nonwoven paper 16*a*, which functions as the filter, can be easily replaced. As a result, it is possible to further reduce the effort for the maintenance of the nonwoven paper 16*a*.

Replacement among a plurality of types of bags 16 having different patterns or colors serves to change the image of a product. As a result, the product's value further rises.

Since the opening (not shown) of the bag 16 is openable and reclosable, the nonwoven paper 16*a*, which functions as the filter, can be detached and cleaned. As a result, it is possible to further reduce the effort for the maintenance of the nonwoven paper 16*a*.

Moreover, using the nonwoven paper 16*a* as the filter allows low manufacturing costs.

The exterior of the bag 16 is easily patterned or colored without a cost increase by printing on the nonwoven paper 16*a*. That is to say, a bag design is easily improved.

Second Embodiment

Figure 3:
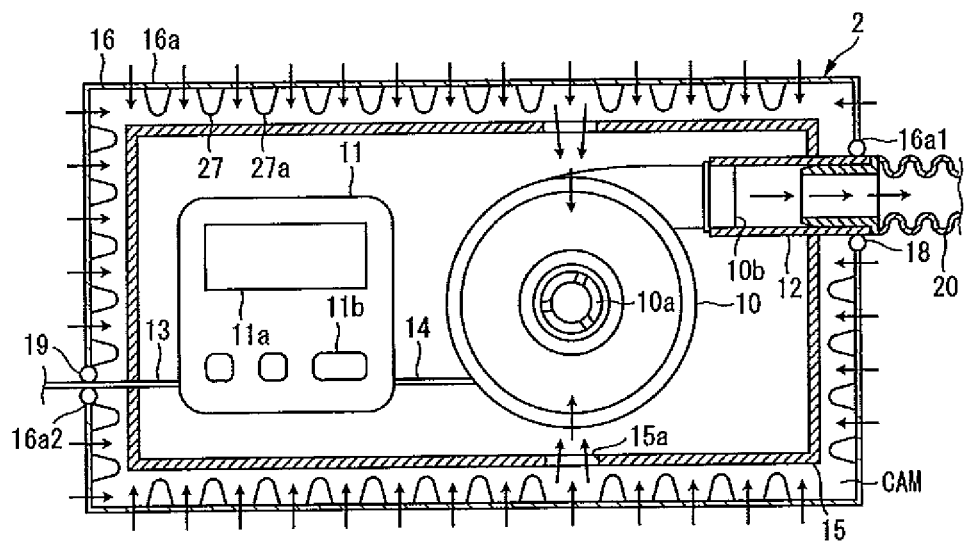
FIG. 3 is a schematic view illustrating the inside of a respiratory assistance device that adopts a filter structure according to a second embodiment of the present invention.

Next, the structure of a respiratory assistance device 2 that adopts a filter structure according to an embodiment of the present invention will be described with reference to FIG. 3. FIG. 3 is a schematic view illustrating the inside of the respiratory assistance device 2. Note that, only characteristic portions of the respiratory assistance device 2 will be described here, though a description about the same structures, effects, and advantages as the respiratory assistance device 1 will be appropriately omitted. Also in each of embodiments described below, only characteristic portions will be described, though a description about the same structures, effects, and advantages as the other respiratory assistance device will be appropriately omitted.

The respiratory assistance device 2 illustrated in FIG. 3 is different from the respiratory assistance device 1 according to the first embodiment in terms of providing a chamber forming member 27, instead of the chamber forming member 17.

The chamber forming member 27 is constituted by a plurality of projections 27*a* attached to the inside of the bag 16.

Third Embodiment

Figure 4:
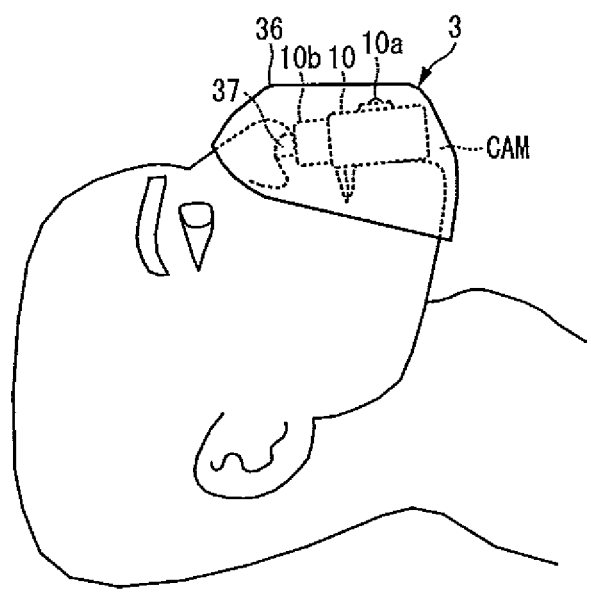
FIG. 4 is a schematic view illustrating the inside of a respiratory assistance device that adopts a filter structure according to a third embodiment of the present invention.

Next, the structure of a respiratory assistance device 3 that adopts a filter structure according to an embodiment of the present invention will be described with reference to FIG. 4. FIG. 4 is a schematic view illustrating the inside of the respiratory assistance device 3.

The respiratory assistance device 3 illustrated in FIG. 4 is provided with a blower 10, a control box (not shown), a mask 36, prongs 37, and the like.

The blower 10 is attached to the inside of the mask 36. That is, the blower 10 is disposed in a chamber CAM formed between the mask 36 and a face of a patient. A gas suction opening 10*a* of the blower 10 takes in gas present in the chamber CAM.

The control box (not shown) is provided outside the mask 36 in an independent manner. A control unit in the control box is electrically connected to a motor (not shown) of the blower 10 through a connection code (not shown).

The mask 36 is fixed on the face of the patient using a fixture such as a band (not shown). The mask 36 covers a mouth or nose of the patient so as to form the chamber CAM between the face of the patient and the mask 36. The mask 36 is made of a filter such as a nonwoven paper. It is noted that at least part of the mask 36 may be formed of the filter. The mask 36 may be appropriately provided with a frame or the like for reinforcement. The mask 36 does not pass gas except for the portion of the filter.

An air feed opening 10*b* of the blower 10 is connected to proximal ends of the prongs 37, and distal ends of the prongs 37 are inserted into the nose of the patient. The prongs 37 lead the gas fed from the air feed opening 10*b* of the blower 10 to the nose of the patient.

Note that, the respiratory assistance device 3 may be provided with a chamber forming member that is disposed between the blower 10 and the mask 36 to maintain the chamber CAM between the gas suction opening 10*a* of the blower 10 and a filter portion of the mask 36. The chamber forming member may be provided outside the blower 10 or inside the mask 36.

Next, a gas flow in the respiratory assistance device 3 will be described with reference to FIG. 4.

Upon operating the blower 10, gas outside the mask 36 is taken into the chamber CAM formed inside the mask 36 through the mask 36. The gas taken into the chamber CAM is taken into the blower 10 through the gas suction opening 10*a*. The gas taken into the blower 10 is compressed and supplied to the respiratory organs of the patient through the air feed opening 10*b*, the prongs 37, and the like.

Fourth Embodiment

Figure 5:
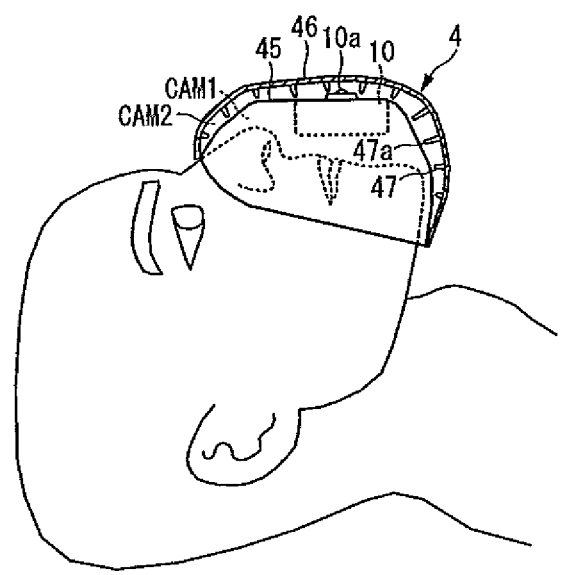
FIG. 5 is a schematic view illustrating the inside of a respiratory assistance device that adopts a filter structure according to a four embodiment of the present invention.

Next, the structure of a respiratory assistance device 4 that adopts a filter structure according to an embodiment of the present invention will be described with reference to FIG. 5. FIG. 5 is a schematic view illustrating the inside of the respiratory assistance device 4.

The respiratory assistance device 4 illustrated in FIG. 5 is provided with a blower 10, a control box (not shown), a mask 45, a cover 46, a chamber forming member 47, and the like.

The blower 10 is provided in the mask 45. A gas suction opening 10*a* is disposed so as to face the outside of the mask 45. This gas suction opening 10*a* takes in gas from the outside of the mask 45. An air feed opening 10*b* is disposed so as to face the inside of the mask 45. This air feed opening 10*b* feeds the gas to the inside of the mask 45. The blower 10 compresses the gas taken by the gas suction opening 10*a*, and supplies the compressed gas to the respiratory organs of the patient through the inside of the mask 45.

The mask 45 covers a mouth or nose of the patient so as to form a chamber CAM1 between a face of the patient and the mask 45.

The cover 46 covers the mask 45. At least part of the cover 46 is formed of a filter (having no reference numeral) such as a nonwoven paper. Note that, the cover 46 does not pass gas except for the portion of the filter.

The chamber forming member 47 is disposed between the mask 45 and the cover 4 so as to form a chamber CAM2 between the gas suction opening 10a of the blower 10 and the filter (having no reference numeral) constituting the cover 46. The chamber forming member 47 is constituted by a plurality of projections 47a attached to the inside of the cover 46.

Next, a gas flow in the respiratory assistance device 4 will be described with reference to FIG. 5.

Upon operating the blower 10, gas outside the cover 46 is taken into the chamber CAM2 formed inside the cover 46 through the cover 46. The gas taken into the chamber CAM2 is taken into the blower 10 through the gas suction opening 10a. The gas taken into the blower 10 is compressed and supplied to the respiratory organs of the patient through the air feed opening 10b, the chamber CAM1, and the like.

Fifth Embodiment

Figure 6:
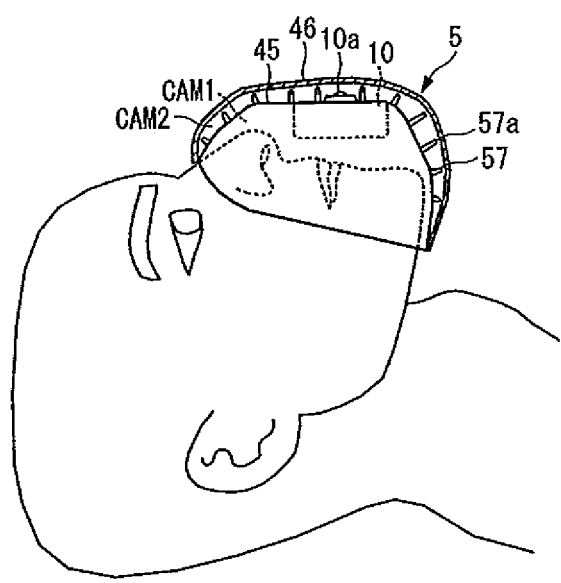
FIG. 6 is a schematic view illustrating the inside of a respiratory assistance device that adopts a filter structure according to a fifth embodiment of the present invention.

Next, the structure of a respiratory assistance device 5 that adopts a filter structure according to an embodiment of the present invention will be described with reference to FIG. 6. FIG. 6 is a schematic view illustrating the inside of the respiratory assistance device 5.

The respiratory assistance device 5 illustrated in FIG. 6 is different from the respiratory assistance device 4 according to the fourth embodiment in terms of providing a chamber forming member 57, instead of the chamber forming member 47.

The chamber forming member 47 is constituted by a plurality of projections 47a attached to the outside of the mask 45.

The present invention is not limited to each of the embodiments described above, but can be variously modified within a range without departing from the general meaning and technical thought thereof.

That is to say, in each of the embodiments described above, the position, size (dimensions), shape, material, orientation, and number of each component are changeable in an appropriate manner.

For example, in the above-described first and second embodiments, the bag 16 is not limited to be formed of the nonwoven paper 16a, as long as it is formed of a filter material. For example, the bag 16 may be formed of a nonwoven cloth.

Also, in each of the embodiments described above, the plurality of projections 17a, 27a, 47a, and 57a of the chamber forming members 17, 27, 47, and 57 are not limited to the forms illustrated in the drawings. The chamber forming members 17, 27, 47, and 57 are not necessarily constituted by the plurality of projections 17a, 27a, 47a, and 57a, respectively.

Figure 7A:
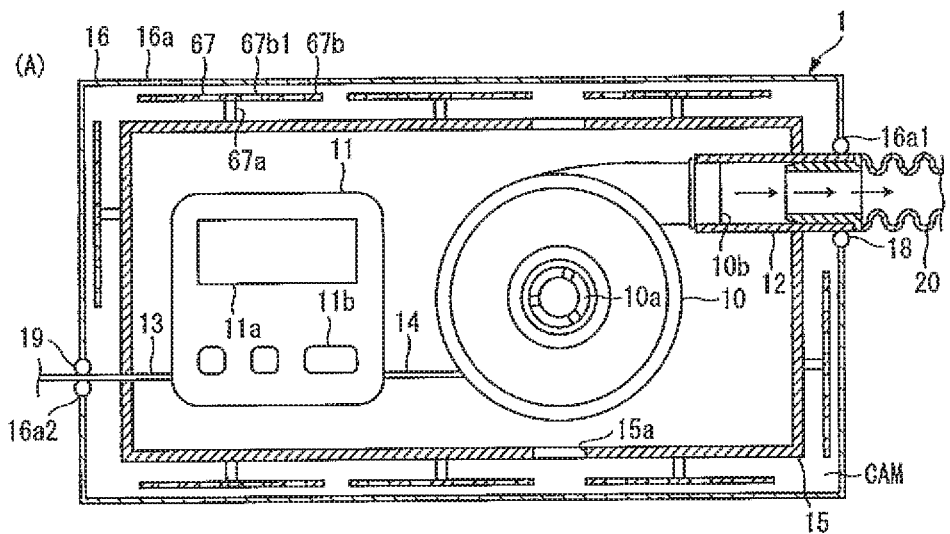
FIGS. 7(A) and 7(B) are schematic views illustrating modified examples of a chamber forming member.
Figure 7B:
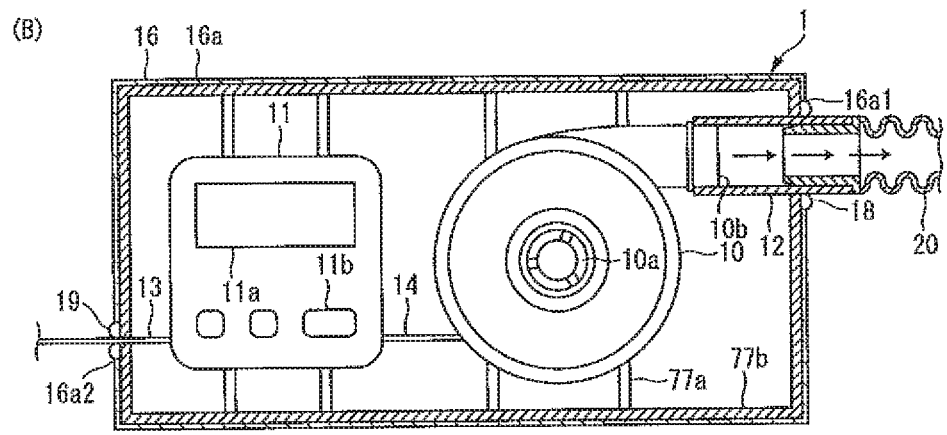

Next, modified examples of the chamber forming member will be described with reference to FIGS. 7(A) and 7(B). FIGS. 7(A) and 7(B) are schematic views illustrating the modified examples of the chamber forming member. Note that, the respiratory assistance device 1 according to the first embodiment is taken as an example.

As illustrated in FIG. 7(A), a first modified example of the chamber forming member is indicated with a reference numeral 67. The chamber forming member 67 includes a plurality of base shafts 67a provided outside the housing 15, and plates 67b provided at tip ends of the plurality of base shafts 67a on a one-by-one basis. Each plate 67b supports the bag 16. In each plate 67b, a plurality of air holes 67b1 are formed.

As illustrated in FIG. 7(B), a second modified example of the chamber forming member is indicated with a reference numeral 77a and 77b. This chamber forming member includes a plurality of base shafts 77a provided outside the blower 10 or the control box 11, and a box-shaped frame 77b provided at tip ends of the plurality of base shafts 77a. The frame 77b is, for example, in a mesh structure (not shown) and has air permeability. The frame 77b supports the bag 16. It is noted that the housing 15 is not provided in this modified example.

Alternatively, the components of each of the above-described embodiments may be applied to the other embodiments if applicable.

For example, the respiratory assistance device 1 according to the first embodiment may be provided with the chamber forming member 27 of the respiratory assistance device 2 according to the second embodiment. That is to say, both of the chamber forming member 17 constituted by the plurality of projections 17a attached to the outside of the housing 15 and the chamber forming member 27 constituted by the plurality of projections 27a attached to the inside of the bag 16 may be provided.

Or, the respiratory assistance device 4 according to the fourth embodiment may be provided with the chamber forming member 57 of the respiratory assistance device 5 according to the fifth embodiment. That is to say, both of the chamber forming member 47 constituted by the plurality of projections 47a attached to the inside of the cover 46 and the chamber forming member 57 constituted by the plurality of projections 57a attached to the outside of the mask 45 may be provided.

The invention claimed is:

1. A filter structure comprising:
   a blower having a gas suction opening, the blower compressing gas taken from the gas suction opening for supplying the compressed gas to respiratory organs of a user;
   a housing that contains the blower within an interior of the housing and has an air passage opening connected to the gas suction opening;
   a bag at least part of which is made of a filter material, the bag covering the housing;
   a chamber forming member disposed between the housing and the bag, the chamber forming member forming a chamber between the air passage opening and the filter material; and
   an air feed pipe that is configured to feed the compressed gas from the blower to the respiratory organs of the user, the air feed pipe being connected to the blower and extending through the housing and the bag;
   wherein the chamber forming member comprises a plurality of projections and the plurality of projections are positioned between the bag and at least two sides of the housing.

2. The filter structure according to claim 1, wherein the filter material is a nonwoven paper.

3. The filter structure according to claim 1, wherein the gas suction opening is for intaking gas that is inside the housing.

4. The filter structure according to claim 1, wherein the chamber forming member is connected to and integrally formed with the housing.

5. The filter structure according to claim 1, wherein the chamber forming member is connected to and integrally formed with the bag.

6. A filter structure comprising:
- a blower having a gas suction opening, the blower compressing gas taken from the gas suction opening for supplying the compressed gas to respiratory organs of a user;
- a housing that encloses the blower therein, the housing having an air passage opening in an exterior surface thereof and connected to the gas suction opening;
- a bag at least part of which is made of a filter material, the bag enclosing the housing; and
- a chamber forming member located between the exterior surface of the housing and an interior surface of the bag, the chamber forming member forming a chamber between the air passage opening and the filter material; and
- an air feed pipe that is configured to feed the compressed gas from the blower to the respiratory organs of the user, the air feed pipe being connected to the blower and extending through the housing and the bag; wherein the chamber forming member comprises a plurality of projections and the plurality of projections are positioned between the bag and at least two sides of the housing.

* * * * *